United States Patent
Zipfel et al.

(10) Patent No.: US 9,295,376 B2
(45) Date of Patent: Mar. 29, 2016

(54) MICROSCOPE APPARATUS, METHOD AND APPLICATION

(75) Inventors: Warren R. Zipfel, Ithaca, NY (US); Rebecca M. Williams, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 262 days.

(21) Appl. No.: 13/992,892

(22) PCT Filed: Dec. 8, 2011

(86) PCT No.: PCT/US2011/063925
§ 371 (c)(1),
(2), (4) Date: Aug. 16, 2013

(87) PCT Pub. No.: WO2012/078853
PCT Pub. Date: Jun. 14, 2012

(65) Prior Publication Data
US 2013/0331653 A1    Dec. 12, 2013

Related U.S. Application Data

(60) Provisional application No. 61/421,008, filed on Dec. 8, 2010, provisional application No. 61/421,437, filed on Dec. 9, 2010.

(51) Int. Cl.
*A61B 1/04* (2006.01)
*G02B 23/24* (2006.01)
(Continued)

(52) U.S. Cl.
CPC ............. *A61B 1/002* (2013.01); *A61B 1/00188* (2013.01); *G02B 21/00* (2013.01); *G02B 21/0012* (2013.01); *G02B 21/06* (2013.01); *G02B 23/2423* (2013.01); *A61B 1/015* (2013.01)

(58) Field of Classification Search
CPC .............. A61B 1/00096; A61B 1/002; A61B 1/00188; A61B 1/015; G02B 23/2423; G02B 23/2446; G02B 23/2438; G02B 21/0028
USPC .......................................... 600/130, 138, 168
See application file for complete search history.

(56) References Cited

U.S. PATENT DOCUMENTS 4,385,810 A * 5/1983 Hamou ......................... 359/381
5,825,502 A * 10/1998 Mayer ........................... 358/296
(Continued)

FOREIGN PATENT DOCUMENTS

GB          703073     *  1/1954
JP       2005334641       12/2005
(Continued)

OTHER PUBLICATIONS

Ahn Jae Yul, International Search Report and Written Opinion; KIPO, Jun. 28, 2012.

*Primary Examiner* — John P Leubecker
(74) *Attorney, Agent, or Firm* — William Greener; Bond, Schoeneck & King, PLLC

(57) ABSTRACT

A microscope apparatus and a microscopic method that uses the microscope apparatus for examining a sample or a specimen, such as but not limited to a tissue sample or a tissue specimen, includes a convex curved distal exit window at a distal end of the microscope apparatus. Due to the presence of the convex curved distal exit window, the microscope apparatus may readily make contact with the sample or the specimen absent trauma to the sample or the specimen. In addition, an index of refraction matched immersion fluid may be used for focusing the microscope apparatus by hydraulic movement of an objective optic lens assembly interior to the distal exit window with respect to the distal exit window. The convex curved distal exit window and index of refraction matched immersion fluid characteristics may be extended to various microscope apparatuses and methods, and in particular medical microscope apparatuses and methods.

22 Claims, 1 Drawing Sheet

(51) Int. Cl.
*G02B 21/00* (2006.01)
*A61B 1/002* (2006.01)
*A61B 1/00* (2006.01)
*G02B 21/06* (2006.01)
*A61B 1/015* (2006.01)

(56) References Cited

U.S. PATENT DOCUMENTS

| | | | | |
|---|---|---|---|---|
| 5,880,880 | A * | 3/1999 | Anderson et al. | 359/385 |
| 5,891,015 | A * | 4/1999 | Strahle | 600/160 |
| 5,968,033 | A | 10/1999 | Fuller et al. | |
| 6,470,124 | B1 * | 10/2002 | Le Gargasson et al. | 385/117 |
| 6,478,730 | B1 * | 11/2002 | Bala et al. | 600/121 |
| 6,530,882 | B1 * | 3/2003 | Farkas et al. | 600/168 |
| 2003/0153812 | A1 * | 8/2003 | Hutchison et al. | 600/168 |
| 2004/0138532 | A1 * | 7/2004 | Glukhovsky | 600/176 |
| 2005/0157981 | A1 * | 7/2005 | Berier et al. | 385/33 |
| 2005/0270664 | A1 * | 12/2005 | Pauker et al. | 359/694 |
| 2007/0244364 | A1 * | 10/2007 | Luanava et al. | 600/160 |
| 2008/0262315 | A1 * | 10/2008 | Inoue | 600/168 |
| 2009/0054791 | A1 | 2/2009 | Flusberg et al. | |
| 2009/0299137 | A1 | 12/2009 | Gal et al. | |
| 2010/0286476 | A1 * | 11/2010 | Jiang et al. | 600/109 |
| 2011/0098530 | A1 * | 4/2011 | Yamane | 600/109 |
| 2011/0118610 | A1 * | 5/2011 | Kuiper et al. | 600/476 |

FOREIGN PATENT DOCUMENTS

| | | | |
|---|---|---|---|
| JP | 2009297409 | A * | 12/2009 |
| JP | 2009297428 | | 12/2009 |

* cited by examiner

MICROSCOPE APPARATUS, METHOD AND APPLICATION

CROSS-REFERENCE TO RELATED APPLICATIONS

This application is related to, and derives priority from, U.S. Provisional Patent Application Ser. No. 61/421,008, filed 8 Dec. 2010, and U.S. Provisional Patent Application Ser. No. 61/421,437, filed 9 Dec. 2010, the contents of which are incorporated herein fully by reference.

BACKGROUND

1. Field of the Invention

Embodiments relate generally to microscope apparatuses, especially as such apparatuses are incorporated into medical instruments such as but not limited to surgical microscopes, laparoscopes, and endoscopes, including but not limited to pharyngoscopes, esophagoscopes, gastroscopes, duodenoscopes, enteroscopes, colonoscopes, sigmoidoscopes, cholangioscopes, rhinoscopes, antroscopes, laryngoscopes, bronchoscopes, nephroscopes, ureteroscopes, cystoscopes, gynoscopes, colposcopes, hysteroscopes, falloposcopes, culdoscopes, arthroscopes, thoracoscopes, mediastinoscoes, coelioscopes, amnioscopes, angioscopes, otoscopes, and ventriculoscopes. Embodiments also relate to nonmedical microscope apparatuses and tools, such as but not limited to benchtop microscope apparatuses and borescope microscope apparatuses, and methods for operation of the microscope apparatuses, such as but not limited to the medical or nonmedical microscope apparatuses.

2. Description of the Related Art

A microscope apparatus may be incorporated into a medical instrument that may be designed specifically for microscopic examination of tissues. Alternative microscope apparatuses may be used in benchtop research or in industrial applications. In the medical field, such microscopic examination of tissues generally senses optical emissions from the tissues. More specifically, multi-photon microscopic examination of tissues via a medical instrument such as a surgical microscope or an endoscope microscope is currently a desirable approach for in vivo imaging of tissues at a level consistent with cellular resolution. However, such multi-photon microscopic examination and imaging of tissues has not necessarily yet been extensively integrated into clinical use.

Thus, desirable are surgical microscope, endoscope microscope, and laparoscope microscope apparatuses and other related medical microscope apparatuses, such as but not limited to laparoscope multi-photon microscope apparatuses and other related multi-photon microscope apparatuses, as well as nonmedical microscope apparatus instruments such as bench top microscope apparatuses and borescope apparatuses, that may be appropriate for integration into clinical use. Also desirable are methods for using the microscope apparatuses, such as but not limited to the laparoscope multi-photon microscope apparatuses and other related multi-photon microscope apparatuses, that may be appropriate for integration into clinical use.

SUMMARY

Non-limiting embodiments are illustrated within the context of, and include, a laparoscope microscope apparatus and a laparoscopic microscopic method that uses the laparoscope microscope apparatus.

While the detailed description as set forth below illustrates the embodiments most specifically within the context of the laparoscope microscope apparatus and the related laparoscopic microscopic method, alternative embodiments are also contemplated that utilize the particular curved distal exit window characteristics, objective optic lens characteristics and objective optic lens configurations in accordance with the laparoscope microscope apparatus and laparoscopic microscopic method. Such additional microscope apparatuses and microscopic methods may include, but are not limited to (especially as such apparatuses are incorporated into medical instruments) surgical microscopes, laparoscopes, and endoscopes, including but not limited to pharyngoscopes, esophagoscopes, gastroscopes, duodenoscopes, enteroscopes, colonoscopes, sigmoidoscopes, cholangioscopes, rhinoscopes, antroscopes, laryngoscopes, bronchoscopes, nephroscopes, ureteroscopes, cystoscopes, gynoscopes, colposcopes, hysteroscopes, falloposcopes, culdoscopes, arthroscopes, thoracoscopes, mediastinoscopes, coelioscopes, amnioscopes, angioscopes, otoscopes, and ventriculoscopes, but also into nonmedical tools such as benchtop microscopes and borescopes.

A non-limiting microscope apparatus in accordance with the non-limiting embodiments includes a curved distal exit window, and in particular a convex curved distal exit window, at a distal objective end of the microscope apparatus. Such a curved distal exit window, and in particular a convex curved distal exit window, better physically stabilizes a sample or a specimen that is contacted by the curved distal exit window of the microscope apparatus in accordance with the non-limiting embodiments and that is imaged while using the microscope apparatus in accordance with the non-limiting embodiments.

Moreover, a non-limiting microscope apparatus in accordance with the non-limiting embodiments may also, or alternatively, include an immersion fluid into which is immersed at least a portion of an objective optic lens assembly interior to the curved distal exit window at the distal objective end of the non-limiting microscope apparatus in accordance with the non-limiting embodiments. This immersion fluid is intended as index of refraction matched with respect to the objective optic lens components within the objective optic lens assembly, and to the sample or the specimen under examination while using the non-limiting microscope apparatus, to thus improve sample imaging properties or specimen imaging properties of the non-limiting microscope apparatus in accordance with the non-limiting embodiments.

With respect to such index of refraction matching, the immersion fluid may assist in increasing an effective imaging depth with respect to a sample or a specimen under examination while using a non-limiting microscope apparatus in accordance with the non-limiting embodiments.

Within the context of focusing a microscope apparatus in accordance with the non-limiting embodiments, the immersion fluid may also be used as a hydraulic fluid that varies a distance of at least one objective optic lens component within an objective optic lens assembly within the microscope apparatus in accordance with the non-limiting embodiments with respect to the curved distal exit window within the microscope apparatus in accordance with the non-limiting embodiments. Such an objective optic lens component to curved distal exit window spacing provides for focus of the microscope apparatus at a particular and specific axial plane in accordance with the non-limiting embodiments.

A microscope apparatus in accordance with the non-limiting embodiments may be designed specifically for, but not necessarily limited to, multi-photon microscopy of samples or specimens, such as for example tissue, in which a contrast mechanism may typically be, but is not necessarily limited to, an intrinsic optical spectroscopic emission from a tissue sample or a tissue specimen intended to be imaged using the microscope apparatus in accordance with the non-limiting embodiments.

A particular microscope apparatus in accordance with the non-limiting embodiments includes a component adapted to transfer light. The particular microscope apparatus in accordance with the non-limiting embodiments also includes at least a connection for a light source located at a proximal end of the component adapted to transfer light. The particular microscope apparatus in accordance with the non-limiting embodiments also includes at least a distal exit window located at a distal end of the component adapted to transfer light. Within the particular microscope apparatus in accordance with the embodiments, the distal exit window has a curvature.

Another particular microscope apparatus in accordance with the non-limiting embodiments includes a component adapted to transfer light. This other particular microscope apparatus in accordance with the non-limiting embodiments also includes a connection for at least a light source located at a proximal end of the component adapted to transfer light. This other particular microscope apparatus in accordance with the embodiments also includes at least a distal exit window located at a distal end of the component adapted to transfer light. This other particular microscope apparatus in accordance with the non-limiting embodiments also includes an objective optic lens assembly located interior to the distal exit window at the distal end of the component adapted to transfer light. Within this particular microscope apparatus in accordance with the non-limiting embodiments, at least one objective optic lens component within the objective optic lens assembly is movable with respect to the distal exit window.

A microscopic method for examining a sample while using a microscope apparatus in accordance with the non-limiting embodiments includes contacting a sample with a distal exit window within a microscope apparatus comprising: (1) a component adapted to transfer light; (2) a light source and a light receiver at a proximal end of the component adapted to transfer light; and (3) the distal exit window at a distal end of the component adapted to transfer light, the distal exit window having a curvature. The microscopic method in accordance with the non-limiting embodiments also includes irradiating the sample with light from the light source while measuring light received at the light receiver.

Another particular microscopic method for examining a sample while using a microscope apparatus in accordance with the non-limiting embodiments includes contacting a sample with a distal exit window within a microscope apparatus comprising: (1) a component adapted to transfer light; (2) a light source and a light receiver at a proximal end of the component adapted to transfer light; (3) the distal exit window at a distal end of the component adapted to transfer light; and (4) an objective optic lens assembly located interior to the distal exit window at the distal end of the component adapted to transfer light. This other particular microscopic method in accordance with the non-limiting embodiments also includes adjusting a focus of the microscope apparatus by adjusting a position of at least one objective optic lens component within the objective optic lens assembly with respect to the distal exit window. This other particular microscopic method in accordance with the non-limiting embodiments also includes irradiating the sample with light from the light source while measuring light received at the light receiver.

Within the non-limiting embodiments, and also within the claims that follow, use of the terminology "proximal" or "distal" is intended as relative terminology indicative of a separation of a component that is proximal from a component that is distal. While the non-limiting embodiments that follow illustrate "proximal" and "distal" components of a non-limiting microscope apparatus within the context of separate ends of a tubular component that comprises a central component adapted to transfer light within a microscope apparatus, the non-limiting embodiments are not intended to be so limited. Rather, the non-limiting embodiments also contemplate "proximal" and "distal" geometric dispositions of components within a non-limiting embodiment that are not necessarily at opposite ends of a tubular component that comprises a central component adapted to transfer light within the microscope apparatus. For example, and without limitation, a proximal component and a distal component with respect to a central component adapted to transfer light within a microscope apparatus in accordance with the non-limiting embodiments may be side mounted to the central component rather than necessarily end mounted to the central component. Moreover, a central component within a non-limiting microscope apparatus in accordance with the non-limiting embodiments need not necessarily be tubular or straight.

BRIEF DESCRIPTION OF THE DRAWING

The objects, features and advantages of the embodiments are understood within the context of the Detailed Description of the Embodiments, as set forth below. The Detailed Description of the Embodiments is understood within the context of the accompanying drawing, which forms a material portion of this disclosure, wherein.

DETAILED DESCRIPTION OF THE EMBODIMENTS

Figure 1A:
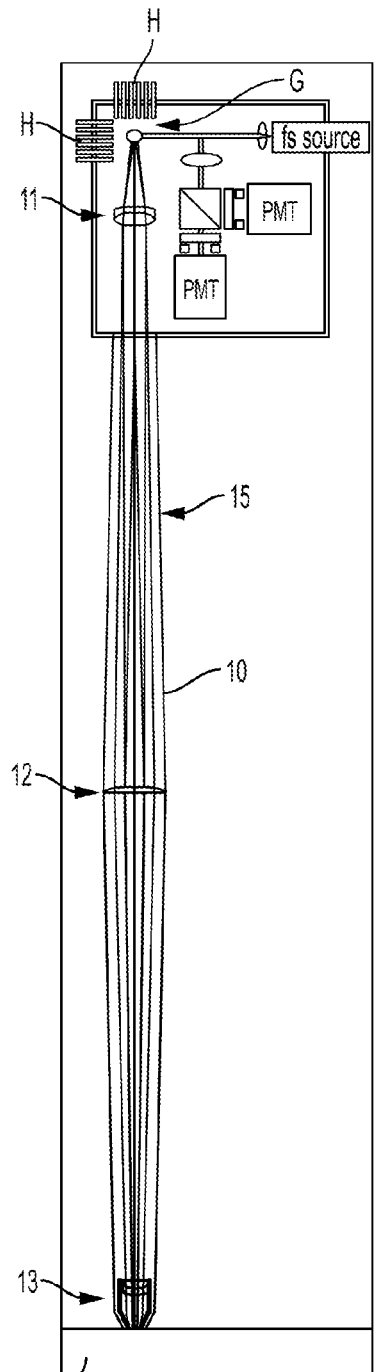
FIG. 1 shows a plurality of schematic cross-sectional diagrams (FIG. 1A, FIG. 1B, FIG. 1C and FIG. 1D) of a laparoscope microscope apparatus and a method for operating the laparoscope microscope apparatus for examining a sample or a specimen, in accordance with the non-limiting embodiments.

The non-limiting embodiments, which include, among other microscope apparatuses and microscopic methods, a laparoscope microscope apparatus and a laparoscopic microscopic method that uses the microscope apparatus, are understood within the context of the detailed description as set forth below. The detailed description as set forth below is understood within the context of the drawing described above. Since the drawing is intended for illustrative purposes, the drawing is not necessarily drawn to scale.

While the detailed description as set forth below illustrates the embodiments most specifically within the context of a laparoscope microscope apparatus and a related laparoscopic microscopic method, alternative embodiments are also contemplated that utilize the particular distal exit window characteristics, objective optical lens characteristics and objective optical lens configurations in accordance with the laparoscope microscope apparatus and the laparoscopic microscopic method in general within additional microscope apparatuses and microscopic methods. Such additional microscope apparatuses and microscopic methods in accordance with the non-limiting embodiments may include, but are not limited to, medical related microscope apparatus instruments such as surgical microscopes, laparoscopes, and endoscopes, including but not limited to pharyngoscopes, esophagoscopes, gastroscopes, duodenoscopes, enteroscopes, colonoscopes, sigmoidoscopes, cholangioscopes, rhinoscopes, antroscopes, laryngoscopes, bronchoscopes, nephroscopes, ureteroscopes, cystoscopes, gynoscopes, colposcopes, hysteroscopes, falloposcopes, culdoscopes, arthroscopes, thoracoscopes, mediastinoscopes, coelioscopes, amnioscopes, angioscopes, otoscopes, and ventriculoscopes. Such additional microscope apparatuses may also include nonmedical microscope apparatus tools such as benchtop microscopes and borescopes and other related microscope apparatuses and microscopic methods.

A laparoscope microscope apparatus (or other related microscope apparatus) in accordance with the non-limiting embodiments in a first instance includes a curved (i.e., typically convex curved) distal exit window, generally at an objective optic lens assembly distal end portion of the laparoscope microscope apparatus in accordance with the non-limiting embodiments. Such a curved distal exit window, which typically comprises a convex curved distal exit window, provides for enhanced contact of the curved distal exit window with a sample or a specimen that is intended to be examined while using the laparoscope microscope apparatus in accordance with the non-limiting embodiments.

A laparoscope microscope apparatus (or other related microscope apparatus) in accordance with the non-limiting embodiments in a second instance may also, or alternatively, include an immersion fluid which is intended as index of refraction matched with respect to the objective optic lens components within the objective optic lens assembly, the distal exit window and the sample or the specimen intended to be examined or imaged using the laparoscope microscope apparatus in accordance with the non-limiting embodiments. Such an immersion fluid may also be used for positioning at least one objective optic lens component within an objective optic lens assembly with respect to the curved distal exit window. In that regard, such an immersion fluid may also serve as a hydraulic fluid, and may comprise an index of refraction matched immersion fluid that is interposed between the curved distal exit window and at least one objective optic lens component within the objective optic lens assembly that is furthest separated from the curved distal exit window within the objective distal end of the laparoscope microscope apparatus in accordance with the non-limiting embodiments.

FIG. 1 shows a plurality of schematic cross-sectional diagrams (i.e., FIG. 1A, FIG. 1B, FIG. 1C and FIG. 1D) illustrating with sequentially enhanced magnification a laparoscope microscope apparatus in accordance with the non-limiting embodiments, as well as a laparoscopic microscopic method for examining a sample or a specimen while using the laparoscope microscope apparatus in accordance with the non-limiting embodiments.

FIG. 1A in particular shows a schematic cross-sectional diagram of a non-limiting laparoscope microscope apparatus in its entirety, and a disposition of the non-limiting laparoscope microscope apparatus with respect to a sample or a specimen in the form of a sample or specimen 20. As is illustrated in FIG. 1A, the sample or specimen 20 may be tissue.

As is illustrated in FIG. 1A, the laparoscope microscope apparatus includes as a central component a tube 10 or related longitudinal hollow structural component adapted to and intended to transfer light (i.e., the central component tube 10 is intended to extend to, or possibly into, the inset box at the top of FIG. 1A, and include a scan lens 11, while also extending to an optical objective 13 end) and having located and assembled at or near a central portion thereof a tube lens 12. Located and assembled at a distal end of the central component tube 10 or related longitudinal hollow structural component is an objective optical lens assembly at the optical objective 13 end which contacts the sample or the specimen 20. At a proximal end (i.e., an upper end) of the central component tube 10 or related longitudinal hollow structural component (i.e., opposite the distal optical objective 13 end) that comprises the laparoscope microscope apparatus in accordance with the non-limiting embodiments, is located and assembled a plurality of components that includes the scan lens 11 (which is particularly illustrated at the middle left hand side of the inset box), stacked galvanometers G, heat sinks H (or alternatively reflective mirrors) as are illustrated in the upper left hand corner of the inset box, detectors (i.e., in the form of photomultiplier tubes PMT) and other components including electronics that are associated with operation of a laparoscope microscope apparatus in accordance with the non-limiting embodiments. Also illustrated within the schematic cross-sectional diagram of FIG. 1A is a femto-second light source (i.e., fs source) that typically, but not exclusively, operates at an excitation wavelength range from about 770 nanometers to about 790 nanometers. Finally, also illustrated within FIG. 1A are light beams 15 at different scan locations within the central component tube 10 that are intended as illustrative of both excitation light from the femto-second source and returned light from irradiation of the sample or specimen 20.

Each of the components assembled to the proximal end of the central component tube 10 or related longitudinal hollow structural component within the laparoscope microscope apparatus in accordance with the non-limiting embodiments as illustrated in FIG. 1A may comprise components that are otherwise generally conventional in the laparoscope microscope apparatus design, assembly and operation art. In that regard, the scan lens 11, galvanometers G, heat sinks H, mirrors, detectors PMT, femto-second source (fs source) and electronics are otherwise generally conventional in the laparoscope microscope apparatus design, assembly and operation art. In addition, the tube lens 12, as well as the central component tube 10 or related longitudinal hollow structural component, is also generally conventional in the laparoscope microscope apparatus design, assembly and operation art.

Typically, the central component tube 10 or related longitudinal hollow structural component will have a length from about 5 to about 100 centimeters, and a cross-sectional diameter from about 2 to about 50 millimeters, and may be formed from any of several conductor materials, insulator materials or composite materials. Specific dimensions of the central component tube 10 or related longitudinal hollow structural component are typically defined within the context of optical characteristics of the scan lens 11 (i.e., within the inset box in FIG. 1A) and the tube lens 12 (i.e., located and assembled within the central component tube 10).

The scan lens 11 and the tube lens 12 are arranged in a 4F configuration, in which the ratio of the tube-lens-focal-length to the scan-lens-focal-length determines an enlargement of an illumination beam cross-sectional area. For optimal image quality the cross-sectional area of the illumination beam should be at least as large as the cross-sectional area of an entrance pupil of an objective optic lens assembly.

Typically, the remainder of the components within the inset box at the proximal end of the central component tube will be properly mated and matched to provide: (1) an optical excitation beam at all locations in the scanned field-of-view through the central component tube 10 to the distal end objective 13 and the sample or specimen 20; and (2) an optical emission beam from the sample or specimen 20 at all locations in the scanned-field-of-view through the distal end objective 13 (i.e., including particular objective optic lens components) and back to the optical detection components within the inset box at the proximal end portion of the central component tube 10.

Figure 1B:
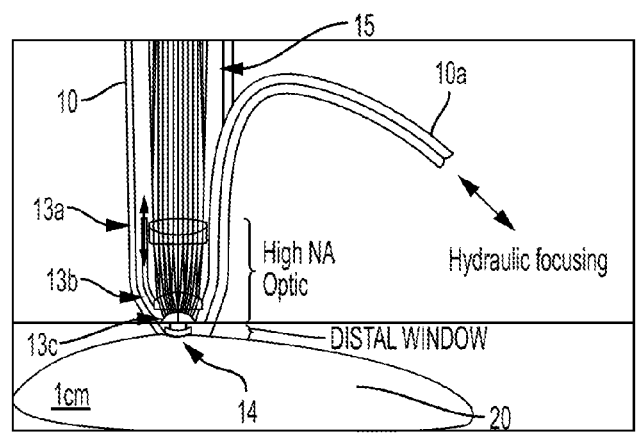

FIG. 1B shows magnified and in greater detail the objective end portion 13 of the laparoscope microscope apparatus in accordance with the non-limiting embodiments, and as illustrated within the schematic cross-sectional diagram of FIG. 1A. As is illustrated in FIG. 1B, the objective end portion 13 comprises a distal exit window 14 which contacts, deflects and deforms a sample or a specimen 20 which is contacted by the distal exit window 14. Given that the distal exit window 14 of the laparoscope microscopic apparatus in accordance with the non-limiting embodiments includes a convex distal exit window 14 curvature, the sample or the specimen 20 when contacted by the distal exit window 14 is less subject to trauma than if, for example, the distal exit window 14 of the laparoscope microscope apparatus in accordance with the non-limiting embodiments comprised a flat shaped planar distal exit window or a concave shaped distal exit window.

FIG. 1B also illustrates an objective optic lens assembly (i.e., designated as a high numeric aperture optic) that is located and assembled interior to the distal exit window 14 at the distal objective end 13 of the central component tube 10 that comprises the laparoscope microscope apparatus in accordance with the non-limiting embodiments. As is illustrated within FIG. 1B, the objective optic lens assembly includes three lenses 13*a*, 13*b* and 13*c* interior to the curved distal exit window 14, where an objective optic lens component 13*a* within the objective optic lens assembly that is furthest separated from the curved distal exit window 14 is intended as retractably movable with respect to the curved distal exit window 14 and the central component tube 10. Such retractable movement of the objective optic lens component 13*a* that is furthest separated from the curved distal exit window 14 is intended as a means to focus the laparoscope microscope apparatus in accordance with the non-limiting embodiments with respect to a desired axial focal plane generally exterior to the curved distal exit window 14 and within the sample or specimen 20.

FIG. 1B also illustrates a particular non-limiting embodiment of an index of refraction matched immersion fluid based hydraulic fluid focusing of the furthest separated objective optic lens component 13*a* with respect to the curved distal exit window 14. As is illustrated within FIG. 1B, the index matched immersion fluid serves as a hydraulic fluid that is injected or otherwise introduced through a port 10*a* in the central component tube 10 into a cavity space interposed between the curved distal exit window 14 and the furthest separated objective optic lens component 13*a* within the objective optic lens assembly with respect to the curved distal exit window 14 (i.e., most typically, the immersion fluid is injected into a cavity space interposed between the furthest separated objective optic lens component 13*a* and the curved distal exit window 14). This injection of the immersion fluid based hydraulic fluid causes the high numeric aperture objective optic lens assembly to be repositioned and repositionable with respect to the curved distal exit window 14 and thus provide for different depths of focus of the laparoscope microscope apparatus in accordance with the non-limiting embodiments.

Figure 1C:
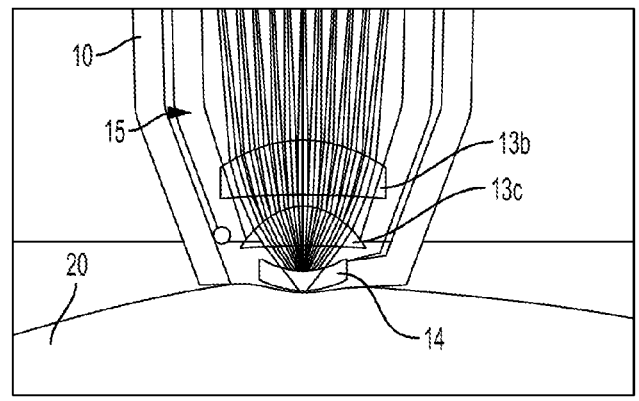

FIG. 1C shows a schematic cross-sectional diagram that illustrates in further magnification contact of the convex curved distal exit window 14 of the laparoscope microscope apparatus in accordance with the non-limiting embodiments within the context of a matching sample or specimen 20 deformation. As is illustrated within the schematic cross-sectional diagram of FIG. 1C, the sample or specimen 20 is deformed and dimpled in a fashion that mates with and matches the convex curved distal exit window 14 of the microscope apparatus. FIG. 1C also illustrates in greater detail the lower lying two generally fixed objective optic lens components 13*b* and 13*c* within the objective optic lens assembly.

As is illustrated within the schematic cross-sectional diagram of FIG. 1C, the sample or specimen 20 is deformed or dimpled absent any deformation of the curved distal exit window 14 in order to assure proper operation of the laparoscope microscope apparatus in accordance with the non-limiting embodiments. Thus, consideration may under certain circumstances be needed to assure that a distal end window is not subject to any deformation that would compromise operation of a laparoscope microscope apparatus in accordance with the non-limiting embodiments. Under certain circumstances other than in-vivo use, a sample or a specimen 20 may be heated to enhance deformation characteristics so that the sample or the specimen 20 deforms in a reasonable time scale in comparison with a curved distal exit window 14 that does not deform, to assure operability of a laparoscope microscope apparatus (or related microscope apparatus) in accordance with the non-limiting embodiments. For reference purposes, deformation of a sample or a specimen 20, may be gauged within the context of deformation of hard clay, where it may be considered that stiffness less than about 10 MPa is desirable.

Figure 1D:
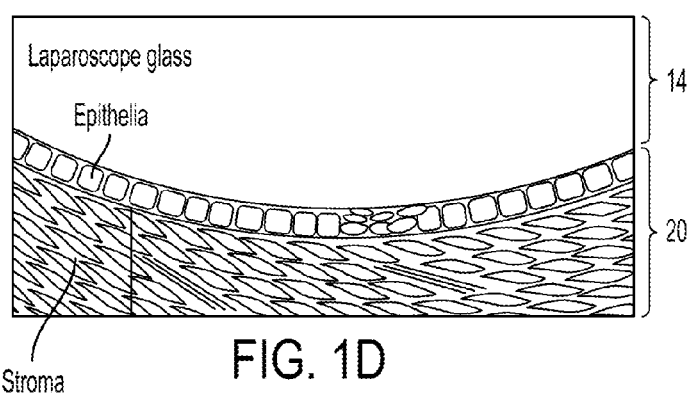

Furthermore, FIG. 1D shows a yet further magnified cross-sectional diagram illustrating the convex curved distal exit window 14 laparoscope microscope glass which makes contact with the sample or specimen 20 surface that, in this example, is tissue that includes underlying stroma cells.

In accordance with the above description of a laparoscope microscope apparatus in accordance with the non-limiting embodiments, the following are relevant considerations with respect to the laparoscope microscope apparatus in accordance with the non-limiting embodiments.

First, for multi-photon imaging applications of a laparoscope microscope apparatus in accordance with the non-limiting embodiments, a point spread function (PSF) quality (i.e., as defined by the compactness of a focused beam quantified by a Strehl ratio >0.9) of the laparoscope microscope apparatus need only be maintained at a design excitation wavelength (i.e., as noted above generally from about 770 nanometers to about 790 nanometers), thus relaxing the optical design criteria for a laparoscope microscope apparatus in accordance with the non-limiting embodiments and enabling a simpler, better performing objective lens assembly.

Second, the design of the laparoscope microscope apparatus in accordance with the foregoing non-limiting embodiments that includes a curved field-of-view within the context of an objective end curved distal exit window is advantageous insofar as for sample imaging or specimen imaging there is no apparent need to constrain an objective end distal exit window to a flat field. In that regard, samples and specimens, for example and without limitation biological tissue samples and biological tissue specimens, are commonly soft and more deformable than typical materials of construction of a distal exit window 14, and a laparoscope microscope apparatus in accordance with the non-limiting embodiments is intended to press against samples and specimens, deforming the samples and the specimens to a curved field-of-view that may match with a Petzval field curvature of the distal curved exit window of the laparoscope microscope apparatus in accordance with the non-limiting embodiments. Thus, a curved distal exit window surface within a laparoscope microscope apparatus in accordance with the non-limiting embodiments serves to stabilize a sample or a specimen against movement based artifacts such as but not limited to subject breathing, and consequently relaxes optical design criteria enabling a wider field-of-view and higher numerical aperture with less optical aberrations in comparison with a lens system that is designed to have a flat field within the context of a flat distal exit window.

Finally, one embodiment for effecting and implementing focusing of the laparoscope microscope apparatus in accordance with the non-limiting embodiments as discussed above is through use of an immersion fluid to provide a variable hydraulic pressure to move at least a portion of the objective optic lens assembly with respect to the distal curved exit window. In an optical design of a laparoscope microscope apparatus in accordance with the non-limiting embodiments, an index matching fluid (i.e., water, glycerol or oil, depending on optical design) may be used as the hydraulic fluid and may be introduced between the objective optic lens assembly (or a component thereof) and the distal exit window of the laparoscope microscope apparatus in accordance with the non-limiting embodiments. Changing the pressure and volume of this index matched fluid that serves as a hydraulic fluid moves the objective optic lens assembly with respect to the tube lens and the curved distal exit window, and optical focusing can be accomplished given the proviso that the two surfaces (i.e., front and back surfaces) of the curved distal exit window are parallel. Insofar as many samples and specimens, especially biological samples and specimens such as tissue, have an optical refractive index closer to water than air, the foregoing design of a laparoscope microscope apparatus in accordance with the non-limiting embodiments enables high numeric aperture optical imaging through several hundred microns of sample or specimen while maintaining a constant average refractive index, thus minimizing spherical aberrations that are normally encountered with increased imaging depth in an air immersion objective optic lens assembly. Other nominally mechanical focusing mechanisms can also be employed (e.g. micrometer facilitated motion of the internal optics relative to the distal exit window) as well within the context of the non-limiting embodiments.

The non-limiting embodiments, describe a multi-photon laparoscope (or other) microscope apparatus design that is optimized for robust in vivo imaging of intrinsic sample or specimen auto-fluorescence and second harmonic generation and of exogenously added contrast agents (for example, acriflavin, fluorescein and indocyanine green (ICG)). Within the context of the foregoing non-limiting embodiments, a laparoscope microscope apparatus length is generally determined by relevant optical characteristics of the scan lens and the tube lens, respectively. An optical design of a laparoscope microscope apparatus in accordance with the non-limiting embodiments is relatively simple. The optical design is optimized only for a relatively narrow excitation source (from about 770 nanometers to about 790 nanometers) and a distal exit window having a curved field-of-view. These relaxations in the optical design criteria enable a high numeric aperture and large field-of-view (FOV) for a laparoscope microscope apparatus in accordance with the non-limiting embodiments with relatively few optical components and elements. The curved distal end window of the laparoscope microscope apparatus contacts samples and specimens and deforms them to adopt the same relaxed field-of-view. This particular design strategy for a laparoscope microscope apparatus in accordance with the non-limiting embodiments enables both a robust optical design and an easy mechanism for finding and stabilizing a micron-scale focal plane. In particular a focus of a laparoscope microscope apparatus in accordance with the non-limiting embodiments may be adjusted by a remote hydraulic mechanism that moves the objective optic lens assembly with respect to the tubular barrel of the laparoscope microscope apparatus and the distal curved exit window of the laparoscope microscope apparatus.

This laparoscope microscope apparatus in accordance with the non-limiting embodiments is designed specifically for in vivo multi-photon microscopy of soft tissue samples and soft tissue specimens, in which the contrast mechanism may comprise (but is not necessarily limited to) intrinsic tissue emissions or second harmonic generation.

A technically complicated operation performed when imaging a sample or specimen with a conventional laser scanning microscope method is to locate an extremely thin focal plane on an irregularly-shaped, macro-sized sample surface or specimen surface. The design of the laparoscope microscope apparatus in accordance with the non-limiting embodiments as described above enables one to merely press against the sample or specimen to locate such a focal plane. For example, one first sets the focusing mechanism of the laparoscope microscope apparatus in accordance with the non-limiting embodiments such that it focuses at the distal surface of the curved distal exit window 14 (for example, the superficial surface of a tissue). Once this primary focus location is located, the objective optic lens component 13a within the objective optic lens assembly may be moved towards the curved distal exit window 14 to further focus in. Additionally, as discussed above, a laparoscope microscope apparatus in accordance with the non-limiting embodiments stabilizes a sample or a specimen to alleviate motions (for example, but not limited to motions due to subject breathing). Depending on the sample or specimen, and on its physical context, an additional clip may provide additional stabilization from behind the sample surface or specimen surface under examination. As long as a design curvature of a field-of-view matches the curvature of both surfaces of the most distal optic, focusing can be accomplished by hydraulically moving the objective lens assembly, which is in a fixed geometric relationship with respect to the curved distal exit window.

The design of laser scanning optical elements is constrained by a wide variety of optical fitness criteria including size, focal plane planarity, distortion, element tolerancing and optical aberrations. Using optical design software, these properties may be largely optimized congruently using automated algorithms. Relaxation of one criterion generally leads to better optimization of the overall fitness function. To achieve the high-quality, high numeric aperture and large field-of-view optical design, an imaged field of view of a sample or a specimen is allowed to curve (i.e., with a radius of curvature in a range from about 5 to about 50 millimeters). Using a design methodology in accordance with the non-limiting embodiments, a laparoscope microscope apparatus (or other microscope apparatus) may be designed with, for example, a width at a distal end of about 1 centimeter, and a numeric aperture from about 0.5 to about 0.9, while maintaining a composite Strehl ratio greater than 0.9 over a field of view that may be greater than about 800 microns.

All references, including publications, patent applications, and patents cited herein are hereby incorporated by reference in their entireties to the extent allowed, and as if each reference was individually and specifically indicated to be incorporated by reference and was set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein is merely intended to serve as a shorthand method of referring individually to each separate value falling within the range, unless otherwise indicated herein, and each separate value is incorporated into the specification as if it was individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

Thus, the non-limiting embodiments are illustrative of the invention rather than limiting of the invention. Revisions and modification may be made to dimensions, structures and materials of composition of a microscope apparatus and related microscopic method in accordance with the non-limiting embodiments, while still providing a microscope apparatus and related microscopic method in accordance with the invention, further in accordance with the accompanying claims.

What is claimed is:

1. A microscope apparatus comprising:
    a component adapted to transfer light;
    a connection for at least a light source located at a proximal end of the component adapted to transfer light;
    at least a distal exit window located at a distal end of the component adapted to transfer light, the distal exit window having a curvature; and
    an objective optic lens assembly located within the distal end of the component adapted to transfer light, and interior to the distal exit window,
   wherein a space interposed between the objective optic lens assembly and the distal exit window is filled with an immersion fluid.

2. The microscope apparatus of claim 1 wherein:
    the curvature is a convex curvature.

3. The microscope apparatus of claim 1 wherein the component adapted to transfer light comprises a hollow tube.

4. The microscope apparatus of claim 3 further comprising:
    a scan lens located at the proximal end of the component adapted to transfer light; and
    a tube lens located at a central portion of the component adapted to transfer light.

5. The microscope apparatus of claim 1 wherein the connection for at least the light source located at the proximal end of the component adapted to transfer light also includes a connection for receiving light from the distal end window.

6. The microscope apparatus of claim 1, wherein the objective optic lens assembly is movable with respect to the distal exit window.

7. The microscope apparatus of claim 1 wherein the immersion fluid is characterized as having an index of refraction matching the objective optic lens components within the objective optic lens assembly and a sample to be examined by the microscope apparatus.

8. The microscope apparatus of claim 1 wherein the objective optic lens assembly that is movable with respect to the distal exit window is positioned by the immersion fluid.

9. A microscope apparatus comprising:
    a component adapted to transfer light;
    a connection for at least a light source located at a proximal end of the component adapted to transfer light;
    at least a distal exit window located at a distal end of the component adapted to transfer light; and
    an objective optic lens assembly located interior to the distal exit window at the distal end of the component adapted to transfer light, where at least one objective optic lens component within the objective optic lens assembly is movable with respect to the distal exit window,
   wherein the objective optic lens assembly is hydraulically movable with respect to the distal end window based upon introduction of an immersion fluid interposed between the movable objective optic lens assembly and the distal exit window.

10. The microscope apparatus of claim 9 wherein:
    the distal exit window has a convex curvature.

11. The microscope apparatus of claim 9 further comprising:
    a scan lens located within the component adapted to transfer light at the proximal end of the component adapted to transfer light; and
    a tube lens located within the component adapted to transfer light at a central region of the component adapted to transfer light.

12. The microscope apparatus of claim 9 wherein the objective optic lens assembly is mechanically movable with respect to the distal exit window.

13. A microscopic method comprising:
    contacting a sample with a distal exit window within a microscope apparatus comprising:
        a component adapted to transfer light;
        a light source and a light receiver at a proximal end of the component adapted to transfer light;
        a scan lens located within the component adapted to transfer light at the proximal end of the component adapted to transfer light;
        a tube lens located within the component adapted to transfer light in a central region of the component adapted to transfer light; and
        an objective lens assembly located within the component adapted to transfer light at the distal end of the component adapted to transfer light and interior to the distal exit window; and
        the distal exit window at a distal end of the component adapted to transfer light, the distal exit window having a curvature;
    irradiating the sample with light from the light source while measuring light received at the light receiver; and
    adjusting the objective optic lens assembly with respect to the distal exit window by means of an immersion fluid interposed between the objective optic lens assembly and the distal exit window to focus the microscope apparatus.

14. The microscopic method of claim 13 wherein:
the distal end window has a convex curvature.

15. The microscopic method of claim 13 wherein the immersion fluid has an index of refraction matched with respect to the objective optic lens assembly and the sample.

16. The microscopic method of claim 15 wherein the sample comprises a soft tissue sample.

17. A microscopic method comprising:
contacting a sample with a distal exit window within a microscope apparatus comprising:
a component adapted to transfer light;
a light source and a light receiver at a proximal end of the component adapted to transfer light;
the distal exit window at a distal end of the component adapted to transfer light; and
an objective optic lens assembly located interior to the distal exit window at the distal end of the component adapted to transfer light;
adjusting a focus of the microscopic apparatus by adjusting a position of at least one objective optic lens component within the objective optic lens assembly with respect to the distal exit window using an immersion fluid interposed between the objective optic lens component and the distal end window; and
irradiating the sample with light from the light source while measuring light received at the light receiver.

18. The microscopic method of claim 17 wherein;
the distal end window has a convex curvature.

19. The microscopic method of claim 17 wherein the microscope apparatus further comprises:
a scan lens located within the component adapted to transfer light at the proximal end of the component adapted to transfer light; and
a tube lens located within the component adapted to transfer light in a central region of the component adapted to transfer light.

20. The microscopic method of claim 17 wherein the adjusting the focus of the microscopic apparatus uses a mechanical adjusting.

21. The microscopic method of claim 17 wherein the immersion fluid is index of refraction matched with respect to the objective optic lens component and the sample.

22. The microscopic method of claim 21 wherein the sample comprises a soft tissue sample.

* * * * *